US006606582B1

(12) United States Patent
Brinkman et al.

(10) Patent No.: US 6,606,582 B1
(45) Date of Patent: Aug. 12, 2003

(54) UNIVERSAL SYSTEM, METHOD AND COMPUTER PROGRAM PRODUCT FOR COLLECTING AND PROCESSING PROCESS DATA INCLUDING PARTICLE MEASUREMENT DATA

(75) Inventors: Matthew James Brinkman, Brush Prairie, WA (US); Joel Wayne Mietzner, Vancouver, WA (US); Marshall Rowe, Chicago, IL (US)

(73) Assignee: SEH America, Inc., Vancouver, WA (US)

( * ) Notice: Subject to any disclaimer, the term of this patent is extended or adjusted under 35 U.S.C. 154(b) by 0 days.

(21) Appl. No.: 09/536,506

(22) Filed: Mar. 27, 2000

(51) Int. Cl.[7] .............................................. G06F 19/00
(52) U.S. Cl. .......................... 702/188; 438/14; 340/500
(58) Field of Search .......................... 700/121; 438/14; 340/870.01, 500; 702/188

(56) References Cited

U.S. PATENT DOCUMENTS

| | | | | |
|---|---|---|---|---|
| 5,598,341 A | * | 1/1997 | Ling et al. .................... | 700/110 |
| 5,625,816 A | * | 4/1997 | Burdick et al. ............... | 379/111 |
| 5,672,230 A | * | 9/1997 | Park et al. ..................... | 134/113 |
| 5,761,064 A | * | 6/1998 | La et al. ........................ | 700/110 |
| 6,177,983 B1 | * | 1/2001 | Trainer ......................... | 356/28.5 |
| 6,223,098 B1 | * | 4/2001 | Cheong et al. ............... | 209/571 |
| 6,233,719 B1 | * | 5/2001 | Hardikar et al. .............. | 716/1 |
| 6,259,101 B1 | * | 7/2001 | Wexler et al. ................. | 250/287 |
| 6,275,290 B1 | * | 8/2001 | Cerni et al. ................... | 356/335 |
| 6,314,379 B1 | * | 11/2001 | Hu et al. ....................... | 700/110 |
| 6,314,385 B1 | * | 11/2001 | Kim et al. ..................... | 700/108 |
| 6,319,737 B1 | * | 11/2001 | Putnam et al. ................ | 438/17 |
| 6,346,983 B1 | * | 2/2002 | Yufa .............................. | 356/338 |

OTHER PUBLICATIONS

Website of Particle Measuring Systems, Inc. at http://www.pmeasuring.com; 20 pages dated Feb. 23, 2000 (Copyright 1998–2000) including Aerosol Manifold, LASAIR® Particle Counter, High Sensitivity Liquid In–Situ System, High Pressure Gas Probe, Aerosol Data Acquisition System and Facility Monitoring System.

* cited by examiner

Primary Examiner—Patrick Assouad
(74) Attorney, Agent, or Firm—Alston & Bird LLP

(57) ABSTRACT

A universal system and method are provided for collecting a plurality of different types of process data, including particle measurement data, from remote locations without requiring manual intervention. The universal system includes a plurality of particle measurement instruments disposed at respective locations distributed about a facility in order to collect particle data. The universal system also includes a process data collection device for providing process data other than particle data, such as temperature, pressure, humidity level, switch position or the like. The universal system further includes a central computer that is located remote from the plurality of particle measurement instruments and from the process data collection device and that is interconnected with the plurality of particle measurement instruments and the process data collection device by means of a computer network. As such, the particle data collected by the respective particle measurement instruments and the other process data collected by the process data collection device can be transmitted across the computer network and received by the central computer that is located remote from the respective locations at which the process data is collected. Advantageously, however, the process data collection device provides the particle data to the central computer in a manner that is independent of the plurality of particle measurement instruments, thereby greatly increasing the flexibility of the system and method. Thereafter, the particle data and the process data can be processed at the central computer.

29 Claims, 4 Drawing Sheets

UNIVERSAL SYSTEM, METHOD AND COMPUTER PROGRAM PRODUCT FOR COLLECTING AND PROCESSING PROCESS DATA INCLUDING PARTICLE MEASUREMENT DATA

FIELD OF THE INVENTION

The present invention relates generally to facility management and control systems and, more particularly, to facility management and control systems and methods for use in the semiconductor wafer manufacturing industry to collect process data including particle measurement data from remote locations.

BACKGROUND OF THE INVENTION

In order to monitor and control modern industrial processes, facility management and control systems have been developed. Facility management and control systems collect various types of process data. A facility management and control system can then analyze the process data for quality control purposes as described below.

The measurement instruments that provide the process data are typically distributed throughout the facility with the particular arrangement dependent upon the nature of the process being monitored and the configuration of the facility. In addition, various types of measurement instruments can be employed depending upon the process data that is to be collected. For example, measurement instruments are typically employed to measure process data such as temperatures, pressures, humidity levels, switch positions and the like. While these measurement instruments can operate independently, the process data provided by the measurement instruments that monitor a particular stage of a process are oftentimes collected by a programmable logic controller.

Although the measurement instruments are typically distributed at various locations throughout the facility depending upon the particular stage of the process that is to be monitored, facility management and control systems generally include a central computer for collecting and processing the data provided by the various measurement instruments. The central computer is typically located at a relatively centralized position, such as within a control room or the like. As such, the central computer is generally remote from most, if not all, of the measurement instruments by being positioned in a different room of the same building or in another building altogether. By collecting the data provided by the measurement instruments or, more commonly, by one or more programmable logic controllers with a central computer, the data can be more thoroughly analyzed such as by cross-checking or correlating the data obtained by measurement instruments that are designed to monitor different stages of the process.

The central computer can process the data in various manners for quality control and other purposes. In this regard, the data can be examined from a historical perspective in an attempt to determine, after the fact, the processing conditions that existed during the fabrication of products that were eventually determined to be of either unusually high quality or unacceptably low quality. In order to avoid fabricating a number of unacceptable products prior to detecting the problem and taking corrective action to bring the process back into tolerance, the central computer can compare the current process data to predetermined acceptable ranges of process data. As such, if the process data collected by the measurement instruments falls outside the predetermined range of acceptable process data, the central computer can trigger an alarm such that the process parameters can be quickly adjusted prior to fabricating a large number of unacceptable products.

One example of a process for which a facility management and control system has been developed is the wafer fabrication process. In this process, wafers, such as silicon wafers, undergo a number of different process steps in order to fabricate wafers having the desired characteristics, such as the desired resistivity, surface roughness, etc. A facilities management and control system that includes a central computer and a number of distributed measurement instruments is particularly useful for a wafer fabrication process since slight variations in the process parameters can substantially alter the characteristics of the resulting wafers, thereby causing wafers that will be unacceptable to be fabricated as a result of only minor changes in the process parameters. A facilities management and control system is also advantageous for a wafer fabrication process since the throughput of a wafer fabrication process is relatively high such that it is desirable to detect variations in the process parameters as soon as possible in order to reduce the number of unacceptable wafers that are fabricated.

In a wafer fabrication process, one of the most important process parameters is the particle count at different stages. In this regard, wafers are subjected to various environments during the fabrication process, some of which are designed to be ultrapure environments having relatively few particles or contaminants. For example, at different stages of the fabrication process, a wafer is typically washed with ultrapure water, exposed to ultrapure chemicals, subjected to high pressure gas, such as hydrogen or nitrogen, having relatively few particles or subjected to an aerosol having relatively few particles, such as within a cleanroom. During any of these stages of the fabrication process, it is desirable to measure the particles in the particular medium, such as the water, chemical, gas or aerosol. As such, various particle measurement instruments have been developed and are commercially available.

Unfortunately, these conventional particle measurement instruments are generally unable to transmit the data, such as the particle counts, that has been collected to a central computer that is remote from the particle measurement instruments in the same manner as other measurement instruments or programmable logic controllers. As such, dedicated computers were oftentimes co-located with the particle measurement instruments in order to collect and characterize the data. In order to correlate the data collected by the particle measurement instruments with the data collected by various other measurement instruments distributed throughout the wafer fabrication facility, technicians would have to manually collect the particle data from the dedicated computers associated with the respective particle measurement instruments distributed throughout the facility, such as by obtaining a printout of the particle data from each dedicated computer or downloading the particle data onto a computer diskette or the like. Typically, the particle data is then manually re-entered into a spreadsheet. By copying other process data from the facilities management and control system, i.e., the process data collected by other measurement instruments, and by exporting this other process data in spreadsheet format, this other process data can be merged with the particle data and the combined data set can be evaluated. As such, the various different types of data collected for the respective stages of the fabrication process can be correlated for training, quality control or other purposes.

As will be apparent, the manual collection and re-entry of the particle data can quickly become time consuming and is subject to errors during the manual re-entry process. As such, attempts have been made to connect the particle measurement instruments to a central computer by utilizing line drivers to transmit the particle data that is provided serially by the particle measurement instruments distributed about the facility to the central computer. Unfortunately, the line drivers are notoriously prone to the introduction of errors, particularly at the relatively high bit rates that would be utilized during the transmission of the particle data.

A facility monitoring system has been developed by Particle Measuring Systems, Inc. (PMS) of Boulder, Colorado that permits the particle data collected by PMS particle measurement instruments to be transmitted to a central computer via a computer network by using TCP/IP protocol. In addition to transmitting the particle data, the PMS particle measurement instruments generally include ports to which other measurement instruments can be connected. The PMS particle measurement instruments can therefore transmit the process data collected by these other measurement instruments along with the particle data to the central computer. For example, measurement instruments that can be connected to a PMS particle measurement instrument include a temperature sensor, a pressure gauge and the like.

Unfortunately, the PMS facility monitoring system does not interface with the measurement instruments of other vendors and therefore does not permit the process data collected by the measurement instruments of other vendors to be transmitted via the computer network for collection by the central computer. In addition, the central computer of a PMS facility monitoring system does not interface with measurement instruments designed to measure process data other than particle data unless these other measurement instruments are first connected to a PMS particle measurement instrument, and the process data collected by these other measuring instruments are transmitted along with the particle data by the PMS particle measurement instrument. Thus, the PMS facility monitoring system does not permit measurement instruments that are independent of the PMS particle measurement instruments to separately transmit process data, such as temperatures, pressures, humidity levels, switch positions or the like, via the computer network to the central computer for processing and correlation with the particle data provided by the PMS particle measurement instruments. As such, it would be desirable to provide a facilities management and control system and method that included a central computer that could universally communicate in a reliable manner with a variety of measurement instruments, including particle measurement instruments, without requiring manual intervention in order to collect and re-enter the particle data and without requiring all process data to be routed through the particle measurement instruments.

SUMMARY OF THE INVENTION

A universal system and method are therefore provided for collecting a plurality of different types of process data, including particle measurement data, from remote locations without requiring manual intervention. In this regard, the universal system includes a plurality of particle measurement instruments, such as aerosol particle monitoring instruments, liquid particle monitoring instruments and gas particle monitoring instruments, disposed at respective locations distributed about a facility in order to collect particle data. The universal system also includes a process data collection device for providing process data other than particle data, such as temperature, pressure, humidity level, switch position or the like. In addition, the universal system includes a central computer that is located remote from the plurality of particle measurement instruments and from the process data collection device and that is interconnected with the plurality of particle measurement instruments and the process data collection device by means of a computer network, such as a local area network and, more preferably, an Ethernet network. As such, the particle data collected by the respective particle measurement instruments and the other process data collected by the process data collection device can be transmitted across the computer network and received by the central computer that is located remote from the respective locations at which the process data is collected. According to the present invention, however, the process data collection device provides the particle data to the central computer in a manner that is independent of the plurality of particle measurement instruments, thereby greatly increasing the flexibility of the system and method. Thereafter, the particle data and the process data can be processed at the central computer.

According to the present invention, the universal system and method for collecting process data permit particle data to be collected at a variety of locations distributed about a facility and then transmitted to and processed by a central computer, typically in near real time, along with various other types of process data. Accordingly, the central computer can correlate the data received from different stages of the process in order to improve the quality control procedure for the respective process.

In order to transmit the particle data via the computer network to a remotely located central computer, the system of the present invention preferably includes a plurality of converters associated with respective particle measurement instruments. Each converter converts particle data that is provided by the respective particle measurement instrument according to a first protocol to a second protocol for transmission via the computer network to a central computer. Typically, the particle measurement instruments provide the particle data serially. As such, the plurality of converters generally convert the serial particle data to TCP/IP for transmission via the computer network to a remotely located central computer. Although the converter can be configured in various manners, the converter of one embodiment is a server such as a microserial server.

Typically, the process data collection device includes a programmable logic controller and a plurality of measurement instruments for collecting different types of process data and for providing the process data to the programmable logic controller. The programmable logic controller can, in turn, provide the process data to the central computer via the computer network in a manner that is independent of the plurality of particle measurement instruments. In this regard, the programmable logic controller as well as the measurement instruments associated therewith are independent of the particle measurement instruments and can therefore provide the process data that has been collected directly to the central computer via the computer network without first routing the process data through a particle measurement instrument.

According to one embodiment to the present invention, a computer program product is provided that processes a plurality of different types of process data collected from various locations distributed about a facility. The computer program product includes a computer readable storage medium, typically accessible by the central computer, that has computer readable program code means. The computer readable program code means includes first computer instruction means for receiving particle data via the computer network from any one of a plurality of particle measurement instruments located at respective remote locations. For example, the first computer instruction means typically receives particle data that is formatted in TCP/IP from any one of the plurality of particle measurement instruments. The computer readable program code means also include second computer instruction means for identifying the respective particle measurement instrument that provides the particle data. In embodiments in which at least one of the particle measurement instruments includes a plurality of measurement ports, the second computer instruction means also identifies the respective measurement port of the particle measurement instrument that provides the particle data. Further, the computer readable program code means includes third computer instruction means for processing the particle data based upon the respective particle measurement instrument identified as providing the particle data. As such, the third computer instruction means can include computer instruction means for generating an alarm that the particle data exceeds a predetermined threshold. In addition, the third computer instruction means can include computer instruction means for identifying trends in the particle data.

According to this embodiment to the present invention, the computer readable program code also includes fourth computer instruction means for separately receiving process data, other than particle data, via the computer network from a process data collection device and fifth computer instruction means for processing the process data. In one embodiment, the computer readable program code means also includes sixth computer instruction means for identifying the respective process data collection device that provides the process data received by the fourth computer instruction means such that the fifth computer instruction means processes the process data based upon the identity of the respective process data collection device.

Therefore, the system, method and computer program product of the present invention permit a plurality of different types of process data to be collected by a plurality of particle measurement instruments and other process data collection devices distributed at various locations about a facility and to then be formatted appropriately and transmitted via a computer network to a remotely located central computer for further processing. Accordingly, the central computer and, in particular, the computer program product operating thereon can collect the particle and other process data in real time or near real time in a manner that eliminates most sources of error such that the particle and other process data can be reliably analyzed for quality control purposes or the like. Thus, the system, method and computer program product of the present invention are particularly well suited for the collection and analysis of particle and other process data during a wafer fabrication process in order to identify process conditions that are out of tolerance prior to the fabrication of a substantial number of unacceptable wafers. By collecting the particle data at a central computer, the central computer and, in particular, the computer program product operating thereon can also correlate the particle data with other process data in a more efficient and reliable fashion in order to identify quality control issues or trends in the data that may need to be corrected.

The system, method and computer program product of the present invention also provides for process data other than the particle data to be provided in a manner that is independent of the particle measurement instruments. As such, the process data collection devices can be located remote from the particle measurement instruments and the process data collection devices can be supplied by different vendors than the particle measurement instruments. The system, method and computer program product of the present invention therefore collects a plurality of different types of process data in a manner that is flexible and that can be easily adapted to many different factory settings.

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
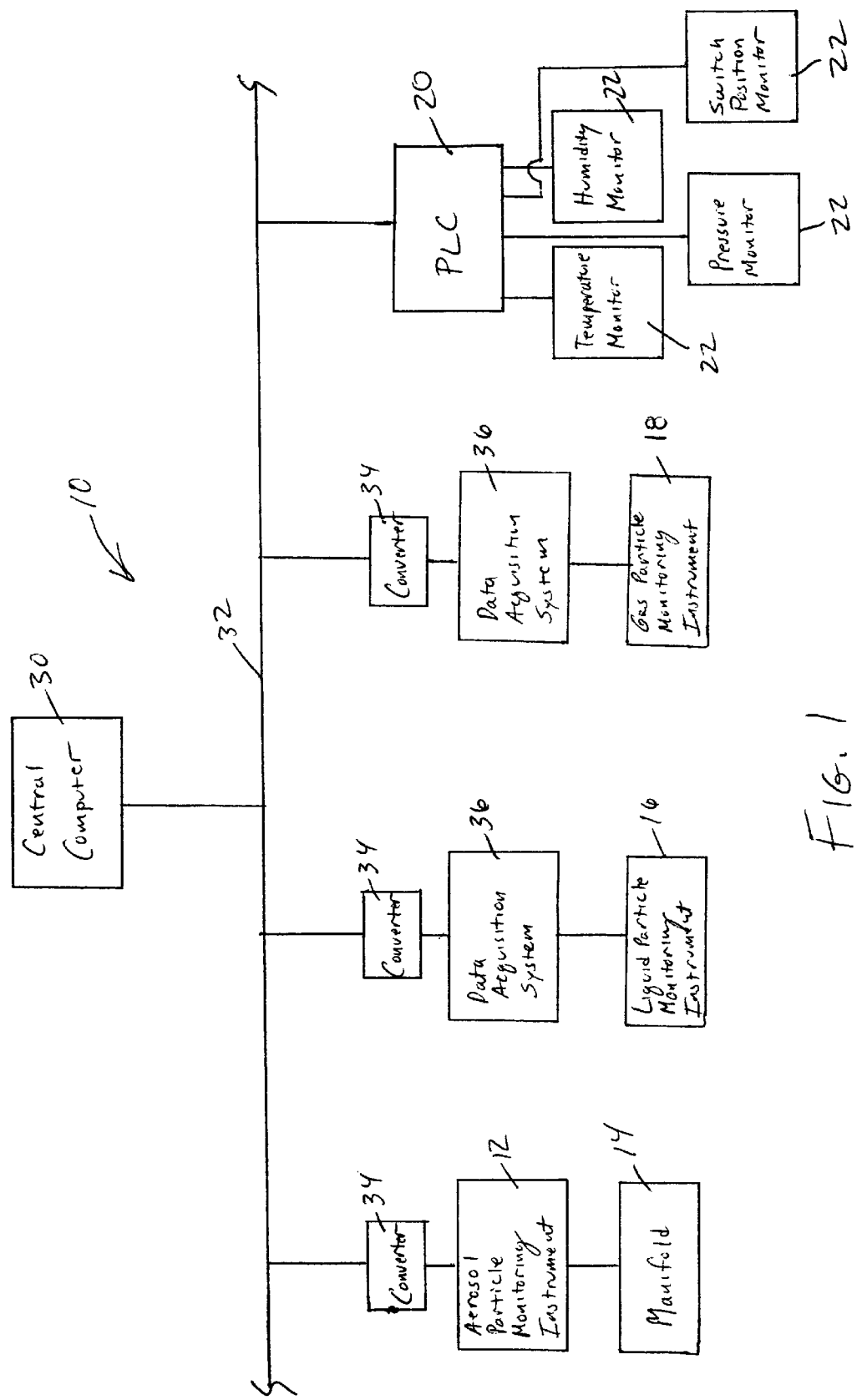
FIG. 1 is a block diagram illustrating a universal system for collecting a plurality of different types of process data, including particle measurement data, according to one embodiment of the present invention.

As depicted in FIG. 1, a system 10 for collecting particle measurement data, from remote locations is provided according to the present invention. While the system, method and computer program product of the present invention can collect process data for various types of processes, the system, method and computer program product of the present invention is particularly well suited for the collection and analysis of a plurality of different types of process data, including particle measurement data, during a wafer fabrication process. For purposes of illustration and not of limitation, therefore, the system, method and computer program product will be subsequently described in conjunction with the collection and analysis of process data, including particle measurement data, during a wafer fabrication process.

The system 10 includes a plurality of particle measurement instruments for collecting particle data. As depicted in FIG. 1, the system can include different types of particle measurement instruments depending upon the environment or the medium in which particles are to be detected. In a wafer fabrication process, for example, it is typically advantageous to detect the particles in several different environments or mediums including the detection of particles in an aerosol such as in a cleanroom, the particles in a liquid, such as ultrapure water or ultrapure chemicals, and the particles in a gas, such as hydrogen or nitrogen, that is generally subjected to relatively high pressure.

As such, the illustrated embodiment of the system 10 includes an aerosol particle monitoring instrument 12, such as a LASAIR® particle counter distributed by Particle Measuring Systems, Inc., for monitoring the particles or contaminants in an aerosol, such as the aerosol stream introduced into a cleanroom. In order to monitor a plurality of points within a cleanroom, the aerosol monitoring instrument can interface with an aerosol manifold 14, such as aerosol manifold Model Nos. AM-12, AM-24 or AM-30 provided by Particle Measuring Systems, Inc. for collecting samples from up to 12, or 24 or 30 locations, respectively, throughout the cleanroom. Thus, a single aerosol particle monitoring instrument can determine the particle count at a plurality of points throughout a cleanroom.

The particle measurement instruments can also include a liquid particle monitoring instrument 16 for monitoring the particles or containments in a liquid, such as ultrapure water or various process chemicals. While various liquid particle monitoring instruments can be employed, one example of a liquid particle monitoring instrument is Model HS-LIS provided by Particle Measuring Systems, Inc. The particle measurement instruments can also include a gas particle monitoring instrument 18 for monitoring the particles or containments in a gaseous environment. In a wafer fabrication process, for example, the gas particle monitoring instrument can monitor the particles in a high-pressure hydrogen and nitrogen environment. While various gas particle monitoring instruments can be employed, one example of a suitable gas particle a monitoring instrument is the high-pressure gas probe provided by Particle Measuring Systems, Inc.

In addition to the particle measurement instrument, the system 10 of the present invention also preferably includes other types of process data collection devices that provide process data other than particle data. For example, the process data collection device may provide process data indicative of the temperature, the humidity level, the pressure, switch positions or the like. Advantageously, the process data collection devices that provide process data other than particle data need not be co-located with the particle measurement instruments, but can be located in other portions of the facility, thereby increasing the flexibility of the system, method and computer program product of the present invention. In addition, the process data collection devices as well as the particle measurement instruments can be supplied by different vendors such that the system, method and computer program product of the present invention provide a universal technique for collecting a plurality of different types of process data from remote locations throughout the facility. In one embodiment, the process data collection device is a programmable logic controller 20 that interfaces with a plurality of measurement instruments 22 for collecting different types of process data. In the illustrated embodiment, for example, the measurement instruments include measurement instruments that monitor the temperature, the pressure, the humidity level and switch positions. However, a process data collection device can include other types of measurement instruments, if so desired.

According to the present invention, the system 10 for collecting various types of process data from remote locations also includes a central computer 30 located remote from the plurality of particle measurement instruments and from the process data collection device. The system also includes a computer network 32 interconnecting the plurality of particle measurement instruments and the process data collection device with the central computer such that the central computer can receive and process the particle data provided by the remotely located particle measurement instruments and the other process data provided by the remotely located process data collection device. Typically, the central computer is located in another portion of the building or, in many situations, in an entirely different building altogether than the particle measurement instruments and the process data collection device. For example, the central computer may be located in a control room or some other computer facility, while the particle measurement instruments and the process data collection device are distributed throughout the facility depending upon the various stages of the process that are monitored.

Typically, the central computer 30 includes a conventional Man-Machine Interface (MMI) package and/or a conventional Supervisory Control And Data Acquisition (SCADA) system, such as Intellusion, Insight, Wonderware, RS-View, Cimplicity or other serial batch type process measurement packages. In the embodiment in which the central computer includes an Intellusion package, the central computer also preferably includes a conventional FIX communications package for supporting communications between the central computer and various measurement instruments distributed about the facility.

With respect to the computer network 32 that interconnects the plurality of particle measurement instruments as well as other process data collection devices to the central computer 30, the computer network is preferably a local area network and, more typically, an Ethernet network. In one embodiment, for example, the Ethernet network is a 1000/100/10 base T Ethernet network. Although the Ethernet network can be constructed in different manners, the Ethernet network typically includes various hardware components, such as switches, routers and the like, interconnected by optical fibers and connected to the particle measurement instruments and the various process data collection devices by electrical cabling. With respect to the electrical cabling, the electrical cables are preferably category 5 cables and higher in order to appropriately transmit the process data, including particle data, throughout the facility.

In order to transmit the particle data via the Ethernet, the particle data provided by the particle measurement instruments is typically converted from one protocol to another. In this regard, the particle measurement instruments typically provide particle data in a serial fashion. In order to transmit the data via the Ethernet network, however, the particle data is preferably converted to a second format, such as TCP/IP. As such, the system 10 of the present invention also preferably includes a plurality of converters 34 for converting the particle data from the first protocol supported by the particle measurement instruments to a second protocol for transmission via the computer network 32. In this regard, the converters can convent the particle data from a serial protocol to TCP/IP for transmission via the Ethernet network. Although a variety of converters can be employed, the converters of one embodiment are servers, such as the microserial servers provided by Lantronix of Irvine, California, for providing the converted particle data to the central computer 30 via the Ethernet network.

In the embodiment depicted in FIG. 1, at least some of the particle measurement instruments, such as the liquid particle monitoring instrument 16 and the gas particle monitoring instrument 18, provide the particle data to a local data acquisition system 36, such as the Data Acquisition System provided by Particle Measuring Systems, Inc. Since each data acquisition system must be located near the respective particle measurement instrument, a different data acquisition system must be co-located with each particle measurement instrument. For those particle measurement instruments that have an associated data acquisition system, the converter 34 can receive the critical data from the data acquisition system and can convert the data to an appropriate protocol, such as TCP/IP, for transmission via the computer network 32.

As described above, the system 10 of the present invention not only collects particle data, but also collects a variety of other types of process data from various locations about the facility. These other types of process data are typically collected by process data collection devices that, in turn, generally include a programmable logic controller 20 and a plurality of measurement instruments 22 for obtaining the different types of process data. As known to those skilled in the art, the programmable logic controllers can interface with a converter to convert the process data to the proper form for transmission via the computer network or, alternatively, the programmable logic controller can be ethernet compatible so as not to require a converter. According to the present invention, the process data collection device also provides the process data to the central computer 30 via the computer network 32. Advantageously, however, the process data collection device provides the process data to the central computer via the computer network in a manner that is independent of the plurality of particle measurement instruments. By being independent of the particle measurement instruments, the process data collection devices need not provide the process data that has been collected by the measurement instruments to the particle measurement instruments for subsequent transmission to the central computer via the computer network. Instead, the process data collection device can be directly connected to the computer network and, in turn, to the central computer. By permitting the process data collection devices to be directly connected to the computer network and, in turn, to the central computer, the process data collection devices need not be positioned at the same locations as the particle measurement instruments. In addition, since the process data collection devices need not communicate with the computer network and, in turn, the central computer via the particle measurement instruments, the process data collection devices and, in particular, the measurement instruments that collect the process data other than the particle data need not be supplied by the same vendor as the particle measurement instruments. Therefore, the system of the present invention provides a relatively universal technique for collecting a plurality of different types of process data from remote locations.

In operation, the plurality of particle measurement instruments collect particle data that is then converted from a first protocol according to which the protocol data is provided by the respective particle measurement instruments to a second protocol, such as TCP/IP. See blocks 40 and 42 of FIG. 2. The converted particle data is then transmitted from the respective particle measurement instrument across a computer network 32, such as an Ethernet network. See block 44. Likewise, the process data collection devices collect process data, other than particle data, from a variety of different measurement instruments 22. The process data is then transmitted by the process data collection devices across the computer network in a manner that is independent of the particle data. The particle and other process data transmitted via the Ethernet network is then received at a central computer 30 that is located remote from the respective locations at which the particle and other process data is collected. See block 46. Thereafter, the particle and other process data can be processed by the central computer. See block 52.

According to one advantageous embodiment of the present invention, the central computer 30 is designed to operate in accordance with a computer program product for processing the particle and other process data collected at a plurality of locations distributed about the facility. The computer program product includes a computer readable storage medium having computer readable program code means embodied therein. According to this embodiment, the computer readable program code means includes first computer instruction means for receiving particle data via a computer network 32 from any one of a plurality of particle measurement instruments located at respective remote locations. See block 46. Typically, the first computer instruction means is designed to receive particle data that is formatted in TCP/IP from any one of a plurality of particle measurement instruments via an Ethernet network.

The computer readable program code means also includes second computer instruction means for identifying the respective particle measurement instrument that provides the particle data that is received. See block 48. In instances in which the particle measurement instrument obtains particle data from a plurality of measurement ports, such as the plurality of measurement ports supported by the aerosol particle monitoring instrument 14 described above, the second computer instruction means also identifies the respective measurement port of the aerosol particle measurement instrument that provides the particle data. Further, the computer readable program code means includes third computer instruction means for processing the particle data based upon the respective particle measurement instrument and identified as providing the data. See block 52. By appropriately identifying the particle measurement instrument that provided the particle data and, in some instances, the measurement port of the particle measurement instrument that provided the particle data, the particular stage of the process to which the particle data relates as well as the type of environment or media from which the particle data was obtained can be determined as described in more detail below.

In a similar fashion to that described above in conjunction with the particle data, the computer readable program code means includes fourth computer instruction means for separately receiving process data, other than particle data, via the computer network 32 from a process data collection device. See block 46. Further, the computer readable program code means includes fifth computer instruction means for processing the process data. See block 52. In order to permit the process data to be processed based upon the respective process data collection device that provided the process data, the computer readable program code means can also include sixth computer instruction means for identifying the respective process data collection device that provides the process data. See block 50. Thus, the fifth computer instruction means can process the process data received from one of the process data collection devices differently than the process data that is received from another process data collection device.

While the computer program product can process the particle data and the other process data in various manners depending upon the process being monitored, the third computer instruction means can include computer instruction means for generating an alarm if the particle data exceeds a predetermined threshold, such as by being outside of a predetermined range of acceptable values. As such, the problem that caused the particle data to exceed the predetermined threshold can be addressed in a timely manner prior to fabricating a number of unacceptable or lower quality products, such as wafers having an undesirably high level of contaminants. In addition, the third computer instruction means can include computer instruction means for identifying trends in the particle data. For example, the particle data can be plotted over time to identify gradual upward, downward or cyclical trends in the particle data that may need to be addressed prior to adversely affecting the quality of the products being fabricated.

Figure 2:
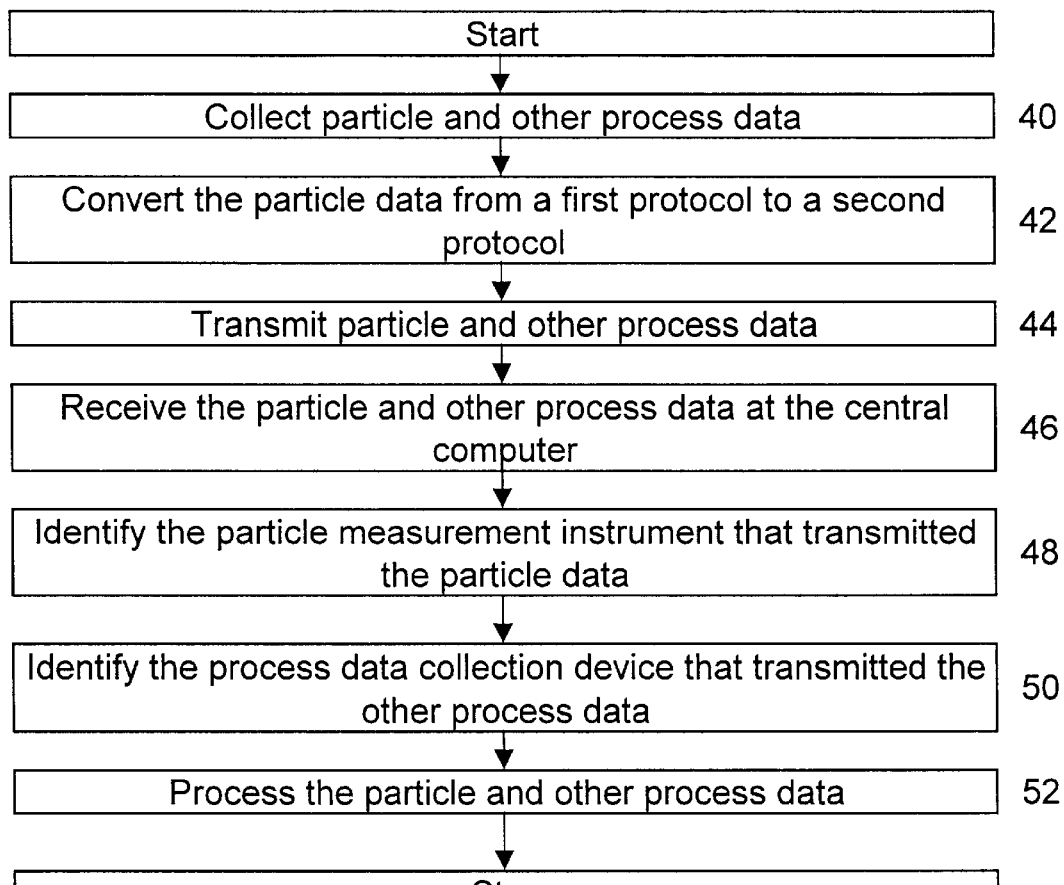
FIG. 2 is a flow chart illustrating operations performed by the system, method and computer program product of one embodiment of the present invention.

In this regard, FIGS. 1 and 2 are block diagram, flowchart and control flow illustrations of methods, systems and computer program products according to the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

In one embodiment in which the system, method and computer program product of the present invention monitor particle data as well as other process data related to a wafer fabrication process, the central computer 30 and, in particular, the computer program product is initially configured to identify or otherwise define each particle measurement instrument and, in instances in which a particle measurement instrument has a plurality of measurement ports, each measurement port of a particle measurement instrument. Typically, the particle measurement instrument is identified by its address on the computer network 32, such as its TCP/IP address, and each measurement port of a particle measurement instrument having a plurality of measurement ports is identified by a manifold number, such as 1 to 30. Thereafter, the particle data will be repeatedly provided by a particle measurement instrument and other process data will be likewise provided by process data collection devices.

In one example, each particle measurement instrument will provide the following data for each sample in the order in which the data is listed.

| Data Elements | Example Designation |
| --- | --- |
| Sample ID | LASAIRID 2 |
| Sample Date | LASAIRDT 2A |
| Sample Time | LASAIRTM 2 |
| Sample Interval | LASAIRINT 2 |
| Sample Volume | LASAIRVOL 2 |
| Sample Version | LASAIRVER 2 |
| Search Mode | SEARCH 2 |
| Manifold Position | MNPOSN 1 |
| Sample Number | SAMPLE 2 |
| Size .10 | SIZE 2A |
| Size .15 | SIZE 2B |
| Size .20 | SIZE 2C |
| Size .25 | SIZE 2D |
| Size .30 | SIZE 2E |
| Size .50 | SIZE 2F |
| Size .70 | SIZE 2G |
| Size 1.00 | SIZE 2H |
| Reference Voltage | REFVLT |
| Air Flow | AIRFLW |
| Analog Value 1 | AV 1 |
| Analog Value 2 | AV 2 |
| Analog Value 3 | AV 3 |
| Analog Value 4 | AV 4 |
| TCP-IP FIX | 151.1.0.82 |
| MANF FIX | 1 |

During the initial configuration process, the operator must also identify each of these data elements that will be provided for a particular sample with an appropriate designation, examples of which are also provided in the above listing. While a number of the data elements are self-explanatory, each will be briefly described herein below for purposes of clarity. "Sample ID" is the name by which a particular sample will be referenced. "Sample Date" and "Sample Time" are the dates and time at which the particle measurement instrument was obtained, while "Sample Interval" is the interval at which the particle measurement instrument repeats the sampling and testing process. "Sample Volume" is the volume of the medium that is sampled and tested by the particle measurement instrument. "Sample Version" is the version of the software that the particle measurement instrument is currently operating. "Search Mode" denotes the manner in which various measurement ports of a particle measurement instrument are searched, such as randomly or in a particular sequence. In addition, "Manifold Position" identifies the particular measurement port through which the sample is obtained. "Sample Number" identifies the number of samples that have been obtained by the particle measurement instrument since the sampling process began. The various sizes represent bins into which the particles are sorted depending upon the size or diameter of the particular particles as measured in microns. For example, the data element "Size 0.10" will be the number of particles in the sample having a diameter of 0.10 microns or less. The "Reference Voltage" and "Air Flow" identify the reference voltage and air flow conditions at the time of obtaining the sample. The "Analog Value"

permit readings from other analog instruments associated with the particle measurement instrument, such as a local temperature sensor, a pressure gauge or the like, to be included along with the particle data for consideration by the central computer 30. Obviously, the process data provided via the analog values is not independent of the process data as described above in conjunction with the process data provided by the process data collection device.

Once the operator has identified or named each of the data elements that will be provided by the particle measurement instrument for each sample, the operator must provide a name for the overall particle measurement instrument. Although the particle measurement instruments can be named in various fashions, the particle measurement instruments are normally named based upon the room or zone of a room in which the particle measurement instrument is located and/or the stage of the process that is being monitored by the particle measurement instrument. An operator must oftentimes also add or identify blocks of memory within the database of the central computer 30 in which the particle data or at least a portion of the particle data will be written. Typically, the blocks of the database are reserved based upon the names by which the respective particle measurement instruments are referenced such that the particle data provided by a respective particle measurement instrument will be stored in a predefined portion of the database maintained by the central computer. Although not described herein, the data elements of the process data provided by the process data collection devices as well as the process data collection devices themselves are typically designated in the same fashion as described above in conjunction with the process data and the particle measurement instruments.

While the communication between the central computer 30 and the plurality of particle measurement instruments and process data collection devices can be designed in various fashions, such as by having the particle measurement instruments and the process data collection devices provide particle data to the central computer in response to polling by the central computer, the particle measurement instruments and the process data collection devices typically provide particle data in an unsolicited fashion. In this regard, the particle measurement instruments and the process data collection devices provide the particle and other process data once the particle and other process data has been collected without awaiting specific request from the central computer for data to be submitted. The central computer therefore preferably includes a plurality of sockets connected to the computer network 32, such as the Ethernet network for receiving particle data from the particle measurement instruments and the process data collection devices. The central computer and, in particular, the first and fourth computer instruction means generally examines each socket in a sequential fashion. If particle or other process data is available at a socket while the central computer is examining the respective socket, the data is received and stored in the database according to the predetermined assignment. In addition to storing the incoming particle or other process data, the central computer can display the data for viewing by an operator. If particle or other process data is delivered to a socket that is not currently being examined by the central computer, the particle or other process data is stored or buffered until the central computer examines the respective socket.

Figure 3:
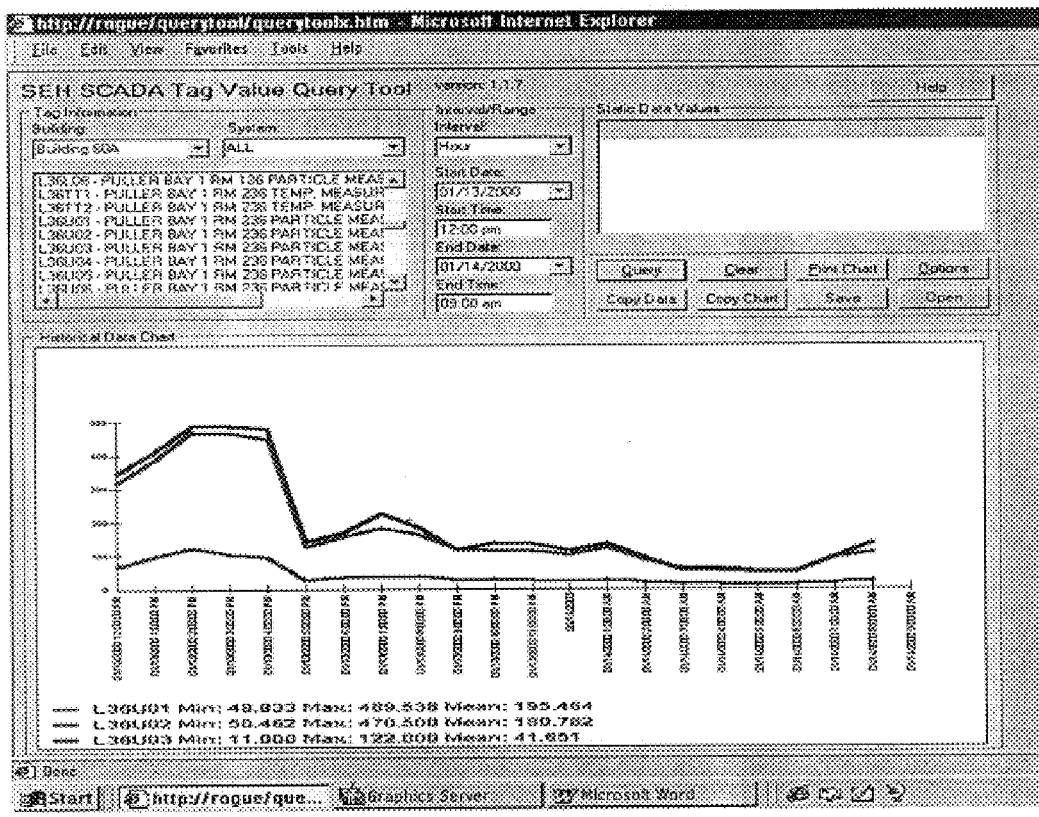
FIG. 3 is a screen display generated by the system, method and computer program product of one embodiment of the present invention illustrating historical trends in the particle data.
Figure 4:
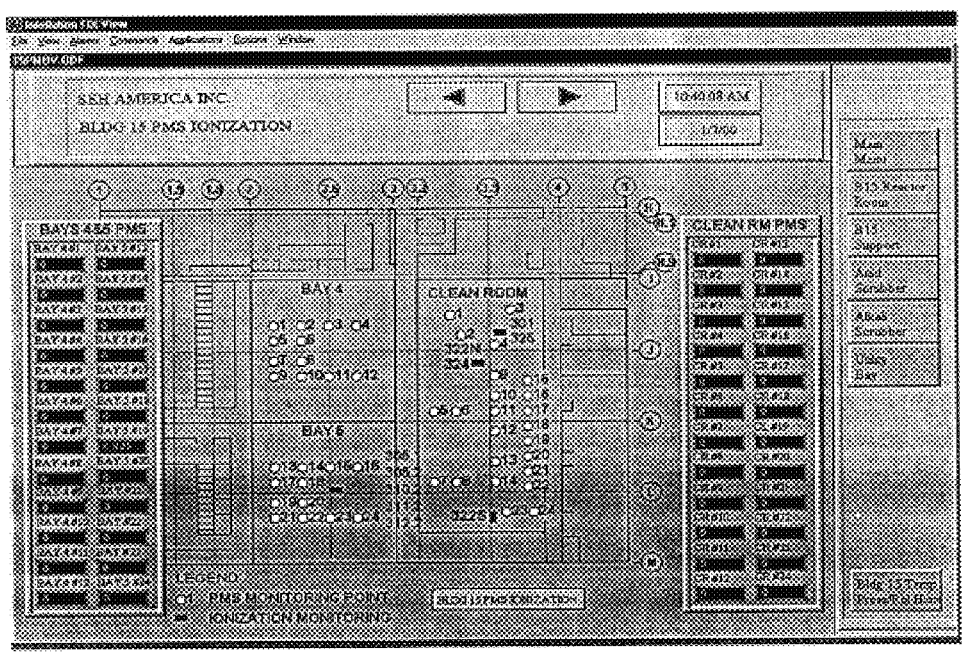
FIG. 4 is a screen display generated by the system, method and computer program product of one embodiment of the present invention illustrating particle counts at various positions within a clean room and within bays 4 and 5.
Figure 5:
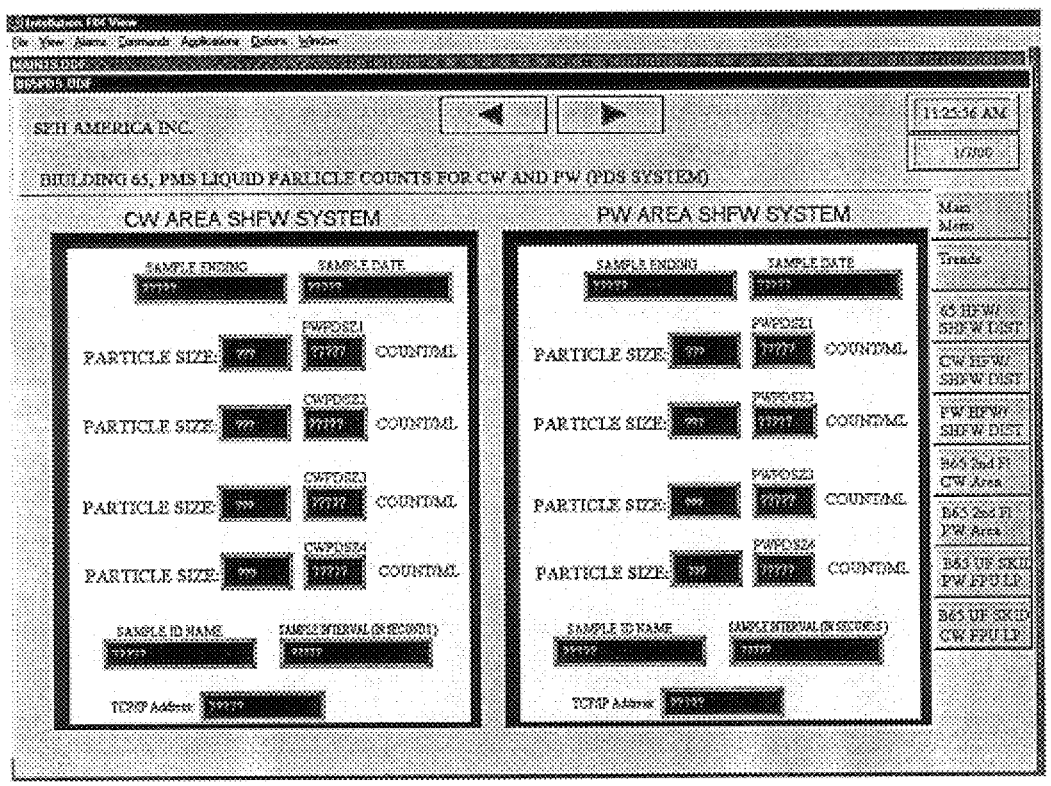
FIG. 5 is a screen display generated by the system, method and computer program product of one embodiment of the present invention illustrating particle counts for particles of different sizes at two stages of the overall process.
Figure 1:
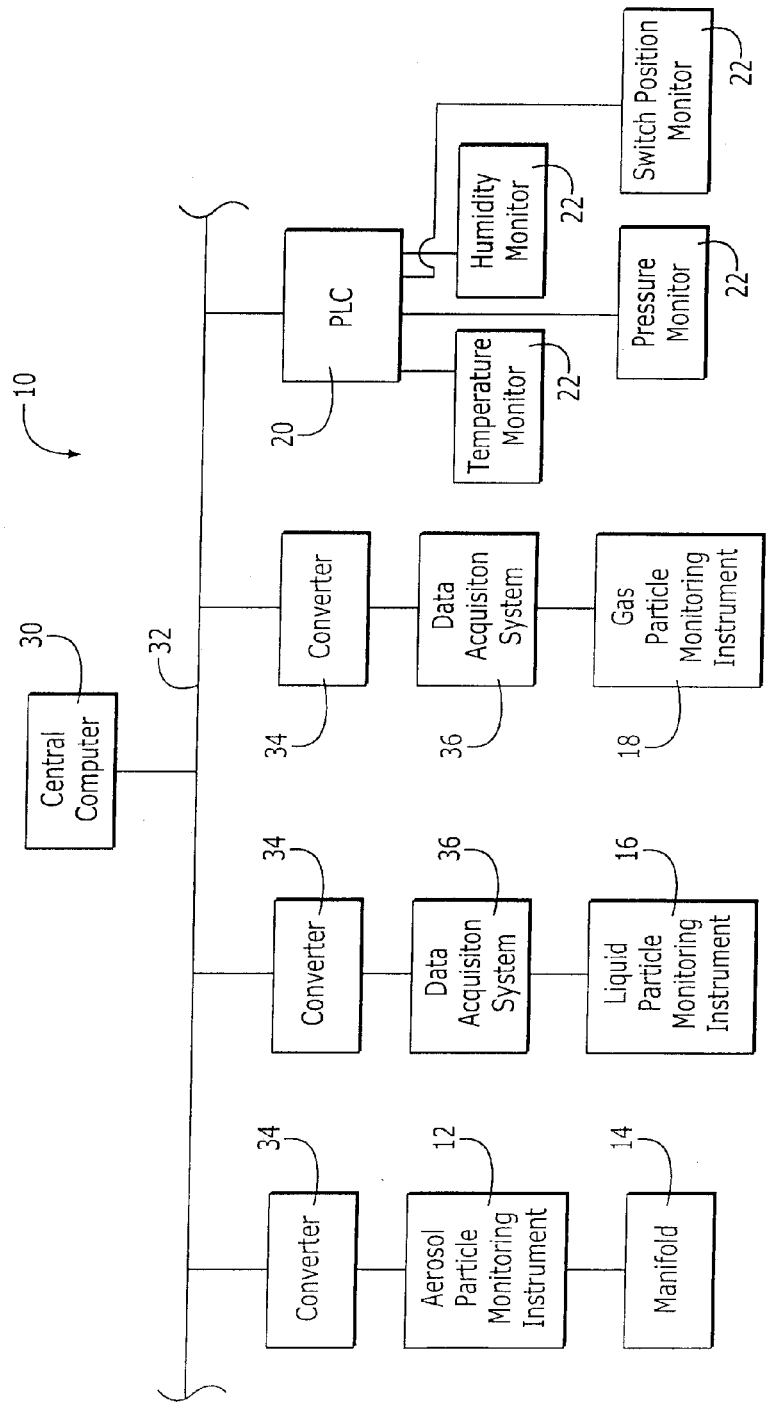
Figure 2:
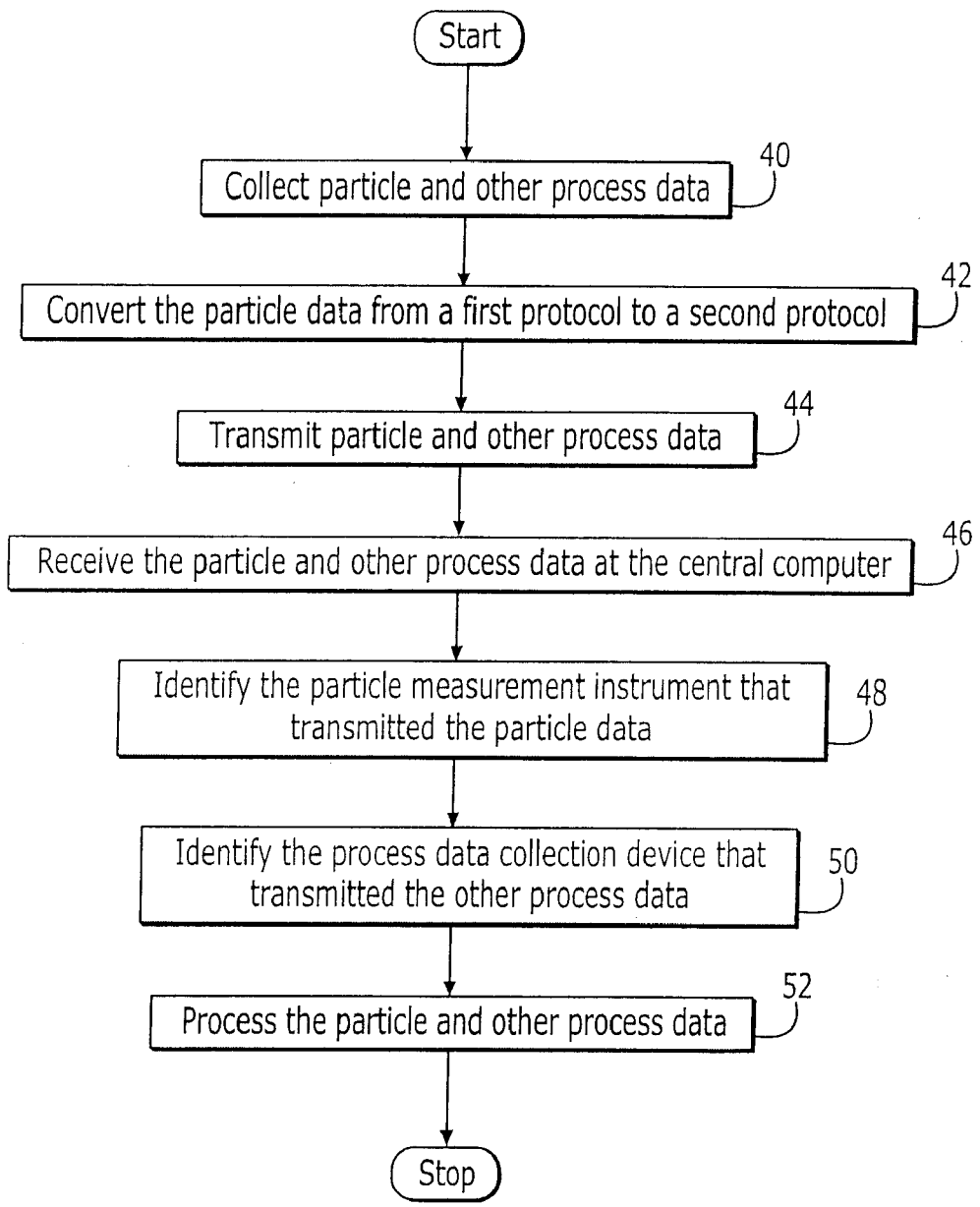
Figure 3:
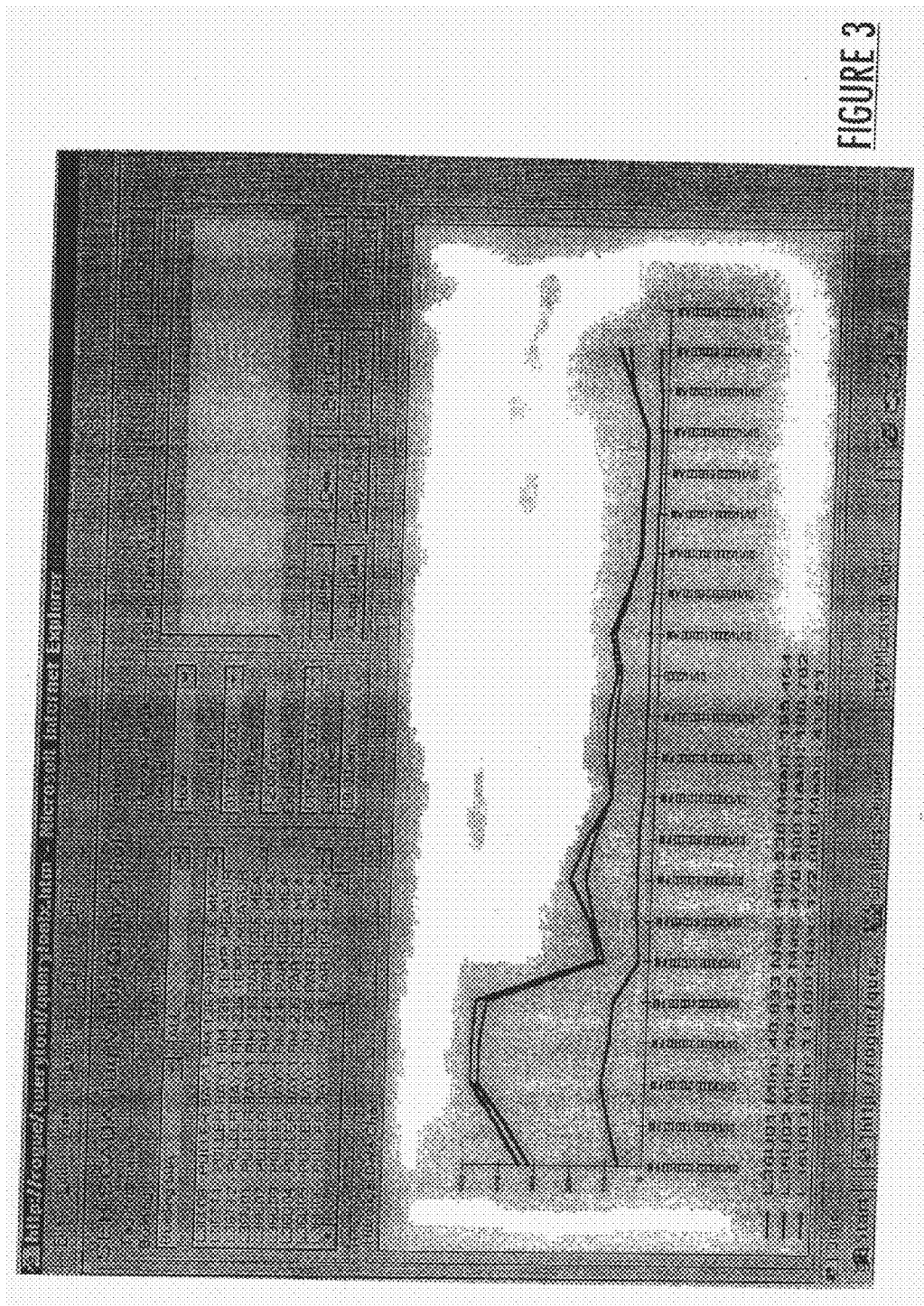
Figure 4:
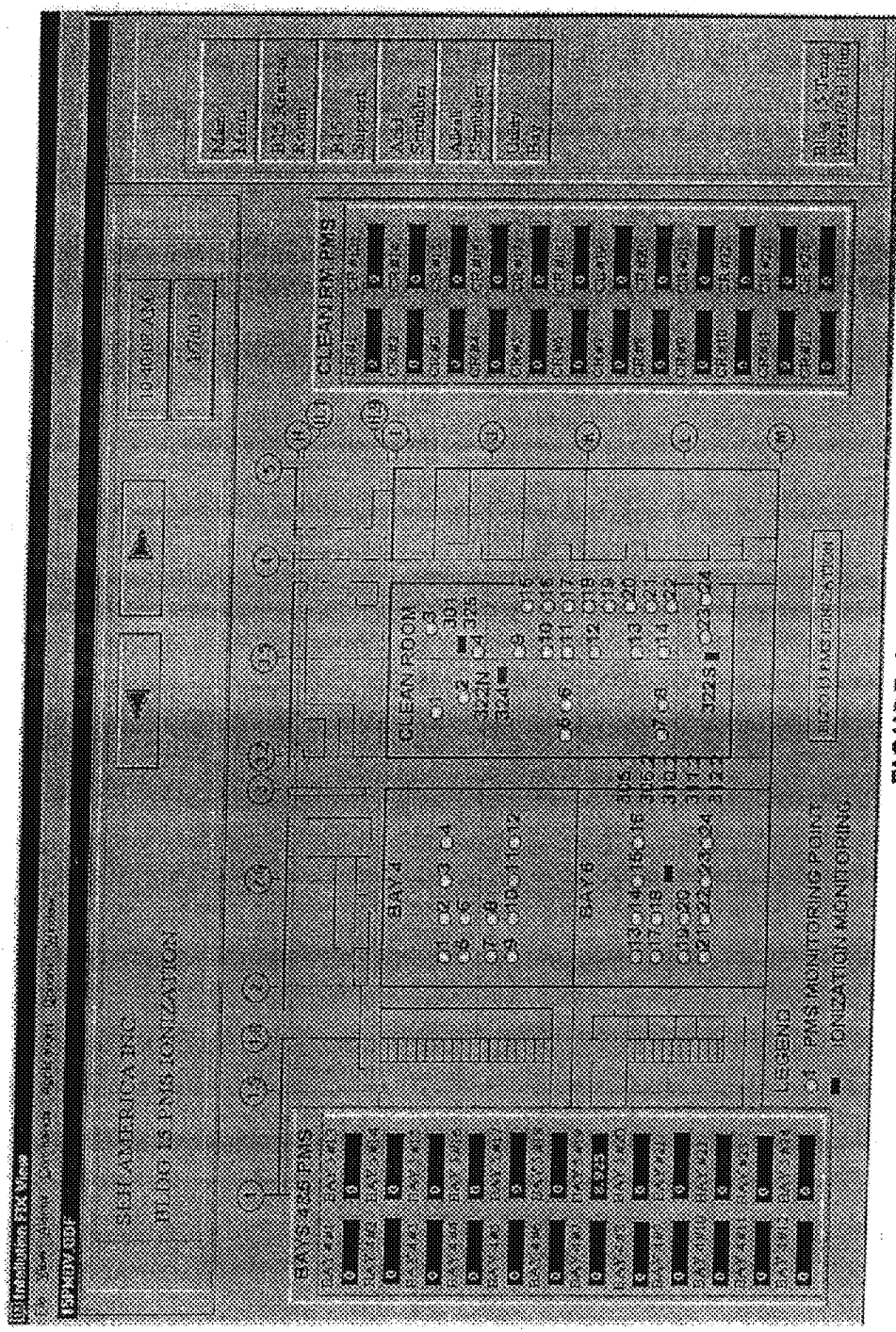
Figure 5:
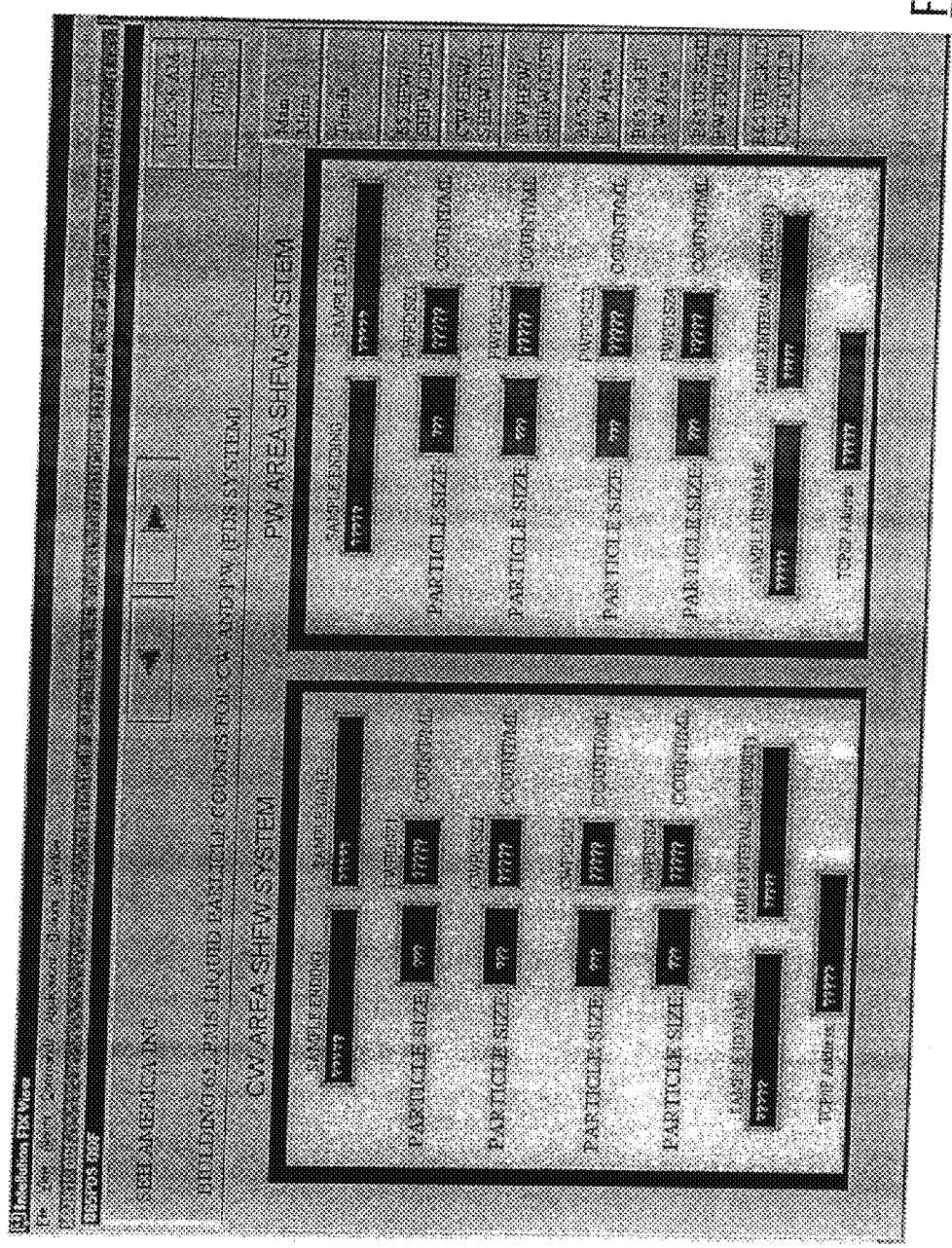

The central computer 30 and, in particular, the third and fifth computer instruction means, can process and display the particle and other process data in various forms. As depicted in FIG. 3, for example, the central computer can display the particle data on a historical basis over a predetermined period of time such that trends in the particle data can be identified and remedial measures taken in order to avoid potential problems in the future without ever allowing the process parameters to become out of tolerance. Alternatively, the particle data can be displayed as depicted in FIG. 4 to provide particle counts for various positions within a cleanroom and within bays 4 and 5 with the display configured to provide the operator with an indication as to the location within the clean room or the bay from which the sample was taken as well as the particle count for the respective location. For purposes of illustration, each particle count is set to 0, although actual particle counts would appear during normal usage. Still further, FIG. 5 depicts a display of particle counts for two different areas of a facility in which the particle counts for particles of four different sizes in each of the two areas is depicted along with the time at which the sample ended, the date of the sample, the sample ID name, the TCP/IP address of the particle measurement instrument and the sample interval. As will be apparent to those skilled in the art, the central computer and, in particular, the third and fifth computer instruction means, can display the particle data in a myriad of other formats depending upon the application and the usage of the particle data without departing from the spirit and scope of the present invention.

Therefore, the system, method and computer program product of the present invention permit a plurality of different types of process data to be collected by a plurality of particle measurement instruments and other process data collection devices distributed at various locations about a facility and to then be formatted appropriately and transmitted via a computer network 32 to a remotely located central computer 30 for further processing. Accordingly, the central computer and, in particular, the computer program product operating thereon can collect the particle and other process data in real time or near real time in a manner that eliminates most sources of error such that the particle and other process data can be reliably analyzed for quality control purposes or the like. Thus, the system, method and computer program product of the present invention are particularly well suited for the collection and analysis of particle and other process data during a wafer fabrication process in order to identify process conditions that are out of tolerance prior to the fabrication of a substantial number of unacceptable wafers.

The system, method and computer program product of the present invention also provides for process data other than particle data to be provided in a manner that is independent of the particle measurement instruments. As such, the process data collection devices can be located remote from the particle measurement instruments and the process data collection devices can be supplied by different vendors. As such, the system, method and computer program product of the present invention collects a plurality of different types of process data in a manner that is flexible and can be easily adapted to many different factory settings.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A universal system for collecting a plurality of different types of process data from remote locations comprising:
a plurality of particle measurement instruments for collecting particle data based upon the particles in a medium to which a wafer is exposed;
a process data collection device for providing process data other than particle data;
a central computer located remote from said plurality of particle measurement instruments and said process data collection device; and
a computer network interconnecting said plurality of particle measurement instruments and said process data collection device with said central computer such that said central computer can receive and process the particle data provided by said plurality of remotely located particle measurement instruments and process data other than particle data provided by said process data collection device, wherein said computer network is capable of buffering at least some of the particle data and the process data prior to receipt and processing by said central computer,
wherein said process data collection device provides the process data to said central computer via said computer network in a manner independent of and without being routed through said plurality of particle measurement instruments.

2. A universal system according to claim 1 wherein said plurality of particle measurement instruments are selected from the group consisting of an aerosol particle monitoring instrument, a liquid particle monitoring instrument and a gas particle monitoring instrument.

3. A universal system according to claim 1 wherein said computer network comprises a local area network.

4. A universal system according to claim 3 wherein said local area network comprises an Ethernet network.

5. A universal system according to claim 1 further comprising a plurality of converters associated with respective particle measurement instruments, each converter adapted to convert particle data that is provided by the respective particle measurement instrument according to a first protocol to a second protocol for transmission via said computer network to said remotely located central computer.

6. A universal system according to claim 5 wherein said computer network is an Ethernet network, and wherein said plurality of converters comprise a plurality of servers for transmitting particle data in the second protocol via said Ethernet network.

7. A universal system according to claim 1 wherein said process data collection device comprises:
a programmable logic controller; and
a plurality of measurement instruments for collecting different types of process data and providing the process data to said programmable logic controller.

8. A universal system for collecting a plurality of different types of process data from remote locations comprising:
a plurality of particle measurement instruments distributed about a facility, each particle measurement instrument adapted to collect particle databased upon the particles in a medium to which a wafer is exposed;
a programmable logic controller for providing process data other than particle data;
a central computer located remote from said plurality of particle measurement instruments and said programmable logic controller;
an Ethernet network interconnecting said plurality of particle measurement instruments and said programmable logic controller with said central computer; and
a plurality of converters associated with respective particle measurement instruments, each converter adapted to convert particle data that is serially provided by the respective particle measurement instrument to TCP/IP for transmission via said Ethernet network to said remotely located central computer,
wherein said programmable logic controller provides the process data other than particle data to said central computer via said Ethernet network in a manner independent of and without being routed through said plurality of particle measurement instruments, and
wherein said Ethernet network is capable of buffering at least some of the particle data and the process data prior to receipt and processing by said central computer.

9. A universal system according to claim 8 wherein said plurality of particle measurement instruments comprise an aerosol particle monitoring instrument.

10. A universal system according to claim 8 wherein said plurality of particle measurement instruments comprise a liquid particle monitoring instrument.

11. A universal system according to claim 8 wherein said plurality of particle measurement instruments comprise a gas particle monitoring instrument.

12. A universal system according to claim 8 wherein said plurality of converters comprise a plurality of servers for transmitting particle data in TCP/IP via said Ethernet network.

13. A universal system according to claim 8 further comprising a plurality of measurement instruments for collecting different types of process data and providing the process data to said programmable logic controller.

14. A method for collecting a plurality of different types of process data from remote locations comprising:
collecting particle data with particle measurement instruments disposed at respective locations distributed about a facility, wherein the particle data that is collected is based upon the particles in a medium to which a wafer is exposed;
collecting process data other than particle data;
transmitting the particle data from the respective particle measurement instruments across a computer network;
transmitting the process data across the computer network in a manner independent of the particle data and without being routed through the particle measurement instruments;
receiving the particle data and the process data transmitted via the computer network at a central computer located remote from the respective locations at which particle data and the process data is collected; and
processing the particle data and the process data at the central computer,
wherein transmitting the particle data and the process data comprises at least one step selected from the group consisting of transmitting the particle data and the process data in response to polling conducted via the computer network and buffering at least some of the particle data and the process data prior to processing of the particle data and the process data at the central computer.

15. A method according to claim 14 wherein said collecting comprises collecting particle data with particle measurement instruments selected from the group consisting of an aerosol particle monitoring instrument, a liquid particle monitoring instrument and a gas particle monitoring instrument.

16. A method according to claim 14 further comprising converting the particle data that is collected from the respective particle measurement instruments in a first protocol to a second protocol prior to transmitting the particle data across the computer network to the remotely located central computer.

17. A method according to claim 16 wherein converting the particle data comprises converting the particle data to TCP/IP prior to transmitting the particle data across the computer network to the remotely located central computer.

18. A method according to claim 14 wherein collecting process data comprises:

collecting different types of process data with a plurality of measurement instruments; and providing the different types of process data to a programmable logic control.

19. A method according to claim 14 wherein said processing comprises generating an alarm if the particle data exceeds a predetermined threshold.

20. A method according to claim 14 wherein said processing comprises identifying trends in the particle data.

21. A computer program product for processing a plurality of different types of process data collected at a plurality of locations distributed about a facility, the computer program product comprising:

a computer readable storage medium having computer readable program code means embodied in said medium, said computer readable program code means comprising:

first computer instruction means for sequentially receiving particle data from respective ports connected via a computer network to respective ones of a plurality of particle measurement instruments located at respective remote locations, wherein said first computer instruction means receives particle data based upon the particles in a medium to which a wafer is exposed;

second computer instruction means for identifying the respective particle measurement instrument that provides the particle data that is received; and third computer instruction means for processing the particle data based upon the respective particle measurement instrument identified as providing the particle data;

fourth computer instruction means for separately receiving process data other than particle data via the computer network from a process data collection device in a manner independent of and without requiring the particle data to be routed through the plurality of particle measurement instruments; and fifth computer instruction means for processing the process data.

22. A computer program product according to claim 21 wherein said first computer instruction means receives particle data that is formatted in TCP/IP from any one of the plurality of particle measurement instruments.

23. A computer program product according to claim 21 wherein at least one particle measurement instrument comprises a plurality of measurement ports, and wherein said second computer instruction means also identifies the respective measurement port of the particle measurement instrument that provides the particle data.

24. A computer program product according to claim 21 further comprising sixth computer instruction means for identifying the respective process data collection device that provides the process data received by said fourth computer instruction means such that said fifth computer instruction means processes the process data based upon the respective process data collection device that provides the process data.

25. A computer program product according to claim 21 wherein said third computer instruction means comprises computer instruction means for generating an alarm if the particle data exceeds a predetermined threshold.

26. A computer program product according to claim 21 wherein said third computer instruction means comprises computer instruction means for identifying trends in the particle data.

27. A universal system according to claim 1 wherein at least one particle measurement instrument comprises a plurality of ports that are each adapted to collect particle data, and wherein said central computer is adapted to receive the particle data from each port of said at least one particle measurement instrument and to identify the port of said at least one particle measurement instrument that collected the particle data.

28. A universal system according to claim 8 wherein at least one particle measurement instrument comprises a plurality of ports that are each adapted to collect particle data, and wherein said central computer is adapted to receive the particle data from each port of said at least one particle measurement instrument and to identify the respective port of said at least one particle measurement instrument that collected the particle data.

29. A method according to claim 14 wherein collecting particle data comprises collecting particle data at a plurality of ports of at least one particle measurement instrument, and wherein processing the particle data comprises identifying the respective port of said at least one particle measurement instrument that collected the particle data.

* * * * *

UNITED STATES PATENT AND TRADEMARK OFFICE
CERTIFICATE OF CORRECTION

PATENT NO. : 6,606,582 B1
DATED : August 12, 2003
INVENTOR(S) : Brinkman et al.

It is certified that error appears in the above-identified patent and that said Letters Patent is hereby corrected as shown below:

<u>Drawings,</u>
Sheets 1-4 should be deleted to be substituted with the attached sheets 1-5, as shown on the attached pages.

Signed and Sealed this

Tenth Day of February, 2004

JON W. DUDAS
*Acting Director of the United States Patent and Trademark Office*